US00PP11893P2

(12) United States Plant Patent
Bak et al.

(10) Patent No.: US PP11,893 P2
(45) Date of Patent: May 29, 2001

(54) GUZMANIA PLANT NAMED 'BOLERO'

(75) Inventors: Elly Bak, Rijsenhout; Nicolaas D. M. Steur, Oude Niedorp, both of (NL)

(73) Assignee: Corn. Bak B.V., Assendelft (NL)

( * ) Notice: Subject to any disclaimer, the term of this patent is extended or adjusted under 35 U.S.C. 154(b) by 0 days.

(21) Appl. No.: 09/244,096

(22) Filed: Feb. 4, 1999

(51) Int. Cl.[7] ..... A01H 5/00
(52) U.S. Cl. ..... Plt./371
(58) Field of Search ..... Plt./371

(56) References Cited

U.S. PATENT DOCUMENTS

P.P. 8,996 * 11/1994 Bak et al. ..... Plt./371

OTHER PUBLICATIONS

GTIM UPOVROM Citation for 'Bolero' as per QZ PBR 971083; Oct. 6, 1997.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new cultivar of Guzmania plant named 'Bolero' characterized by the combined features of a plant form that is funnel-form rosette; plant height of approximately 45 cm when flowering; linear-lanceolate leaves measuring 30–42 cm in length and 3–4 cm in width; leaf color upperside and underside of RHS 147A; primary bract color of RHS 158A and scape bract color of 158A with apices having a color of RHS 147A.

2 Drawing Sheets

The present invention comprises a new and distinct cultivar of Guzmania that is an interspecific hybrid within the genus of Guzmania of the family Bromeliaceae.

BACKGROUND OF THE INVENTION

Guzmania are predominantly epiphytic with a few terrestrial species and are native to the tropics. For the most part species vary in diameter from 7 or 8 inches to 3 or 4 feet and have rosettes of glossy, smooth edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. The plants are generally grown in shade and during the spring to autumn period the central vase-like part of the leaf rosette is filled with water.

Guzmania is native to tropical America. Leaves of Guzmania are usually formed as basal rosettes which are stiff and entire and in several vertical ranks. Guzmania have terminal spikes or panicles which are often bracted with petals united in a tube about as long as the calyx. The ovary is superior and the seeds plumose.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

Methods for cultivation and breeding of Guzmania are well known. For a detailed discussion, reference is made to the following publications, which are incorporated herein by reference. Benzing, David H., THE BIOLOGY OF THE BROMELIADS, Mad River Press, Inc., Eureka (1980); Zimmer, Karl, BROMELIEN, Verlag Paul Parey, Berlin (1986); and Rauh, Werner, BROMELIEN, Verlag Eugen Ulmer, Stuttgart (1981).

The new cultivar 'Bolero' is a product of a planned breeding program in Assendelft, The Netherlands, in 1986. A selection of *Guzmania wittmackii* identified by Code No. 8626202 was crossed with a selection of *Guzmania lingulata minor*, identified by Code No. 8626204. The progeny of this cross were first flowered in 1988.

Asexual propagation of progeny from the cross was first made by off-shoots. Asexual propagation by tissue culture commenced in 1990. The first plants propagated through tissue culture flowered in 1994. The new cultivar 'Bolero' is a naturally occurring whole plant mutation of an unnamed plant from the progeny of the stated cross. The new cultivar 'Bolero' was identified in 1995. The selection was first asexually propagated through tissue culture by, or under the supervision of, the inventors in Assendelft, beginning in 1996. Continuous asexual propagation has demonstrated that the combination of characteristics as herein disclosed for the new cultivar 'Bolero', as observed in Assendelft, the Netherlands, are firmly fixed and are retained through successive generations of asexual reproduction.

'Bolero' has not been tested under all available environmental conditions. The phenotype may vary with variations in environment conditions such as temperature, light intensity, frequency of fertilization, composition of fertilizer, acetylene treatment, day length and humidity without, however, any change in the genotype of the new cultivar.

The closest comparison cultivar is Guzmania 'Salsa' described in U.S. Plant Pat. No. 10,369. The most important difference between these cultivars is that 'Bolero' has a white inflorescene.

BRIEF SUMMARY OF THE INVENTION

'Bolero' is particularly characterized by the following characteristics:

1. Plant form that is a funnel-form rosette;

2. Plant height of approximately 45 cm;

3. Linear-lanceolate leaves measuring 30–42 cm in Length and 3–4 cm in width;

4. Leaf color upperside of RHS 147A and underside of RHS 147A;

5. Primanry bract color of RHS 158A;

6. Scape bract color of RHS 158A; and.

7. Scape bract color apices of RHS 147A.

Guzmania 'Bolero' is a solid, long-lasting hybrid with superior bract-production and a white inflorescence that exhibits good keeping quality.

BRIEF DESCRIPTION OF THE DRAWINGS

The accompanying color photographs show typical inflorescence and foliage characteristics of 'Bolero', with the colors being as true as possible with illustrations of this type. Phenotypic expressions may vary with differences in growth, environmental and cultural conditions without any change in genotype of the cultivar.

Sheet 1 is a side view of a specimen of 'Bolero' showing the primary and floral bracts.

Sheet 2 is a close-up view of floral bracts of 'Bolero'.

DETAILED BOTANICAL DESCRIPTION

The following traits have been repeatedly observed and in combination distinguish 'Bolero' as a new and distinct cultivar. These observations, measurements and descriptions were taken for 'Bolero' plants grown under greenhouse conditions in Assendelft, The Netherlands which approximate those generally used in commercial practice. The new cultivar flowers approximately 15 weeks after treatment with acetylene.

CLASSIFICATION

I. Plant:

*Form*.—Funnel-form rosette.

*Height*.—Approximately 45 cm high (flowering).

*Growth habit*.—Stemless.

*Diameter*.—Approximately 65 cm.

II. Foliage:

*Size of leaf*.—Length: Approximately 30–42 cm. Width: Approximately 3–4 cm.

*Color*.—Upperside: RHS 147A. Underside: RHS 147A. (The color of the leaves can change depending on environmental conditions.)

*Shape*.—Linear-lanceolate.

*Surface texture*.—Smooth.

III. Bracts:

*Length*.—Scape bracts: the lowest are approx. 28 cm long and those just below primary bracts are approx. 10 cm long primary bracts: the lowest are approx. 10 cm long and the upper most primary bracts are approx. 4 cm long.

*Width*.—Scape bracts: Approx. 3.5 cm. Primary bracts: Approx. 3 cm.

*Number*.—Scape bracts: Approx. 11. Primary bracts: Approx. 14.

*General shape*.—Lanceolate.

*Texture*.—Smooth.

*Margin*.—Entire.

*Color*.—Scape bracts: Upper and lower surfaces are RHS 158A; base in green RHS 147A, but may have some light brownish color, RHS 164B, depending on environmental conditions. Scape bract apices: RHS 147A. Primary bracts: Upper and lower surfaces are RHS 158A; base in green, RHS. 147A, but may have some light brownish color, RHS 164B, depending upon environmental conditions; apices are green, RHS 147A.

IV. Flowers:

*Borne* (*stalks*).—Erect.

*Type of inflorescence*.—Compound.

*Size of inflorescence on stalk*.—Approximately 14 cm high.

*Diameter of inflorescence*.—Approximately 24 cm.

*Individual petals*.—(Mostly disposed within the floral bracts and hidden behind the primary bracts.)

*Length*.—Approximately 5 cm.

*Width*.—Approximately 0.5 cm.

*Quantity*.—Approximately 80 flowers divided over approximately 12 branches depending on the size of the plant.

*Color*.—White.

*Time of blooming*.—A fully grown plant can produce an inflorescence containing approximately 80 flowers and can bloom anytime throughout the year starting ±15 weeks after natural induction or induction by treatment with acetylene.

*Duration of blooms*.—Each flower blooms 1 day and the total time of blooming is about 5 weeks.

V. Reproductive organs:

*Ovaries*.—Superior.

*Stamens*.—6 in number.

VI. Seed characteristics: Sterile hybrid therefore no fruit or seed.

*Resistance to disease/pets*.—No observations made.

We claim:

1. A new and distinct cultivar of Guzmania plant, as illustrated and described.

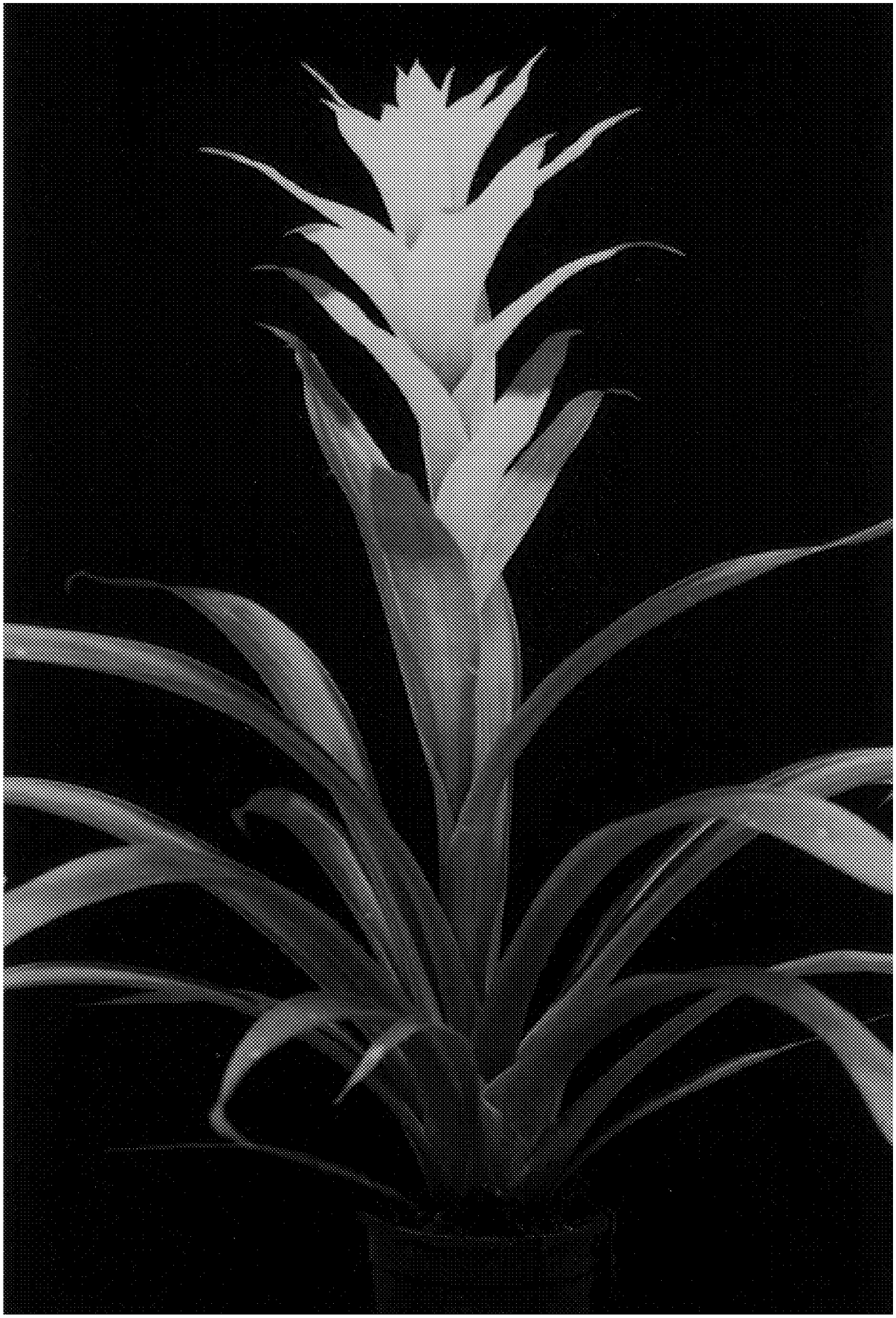

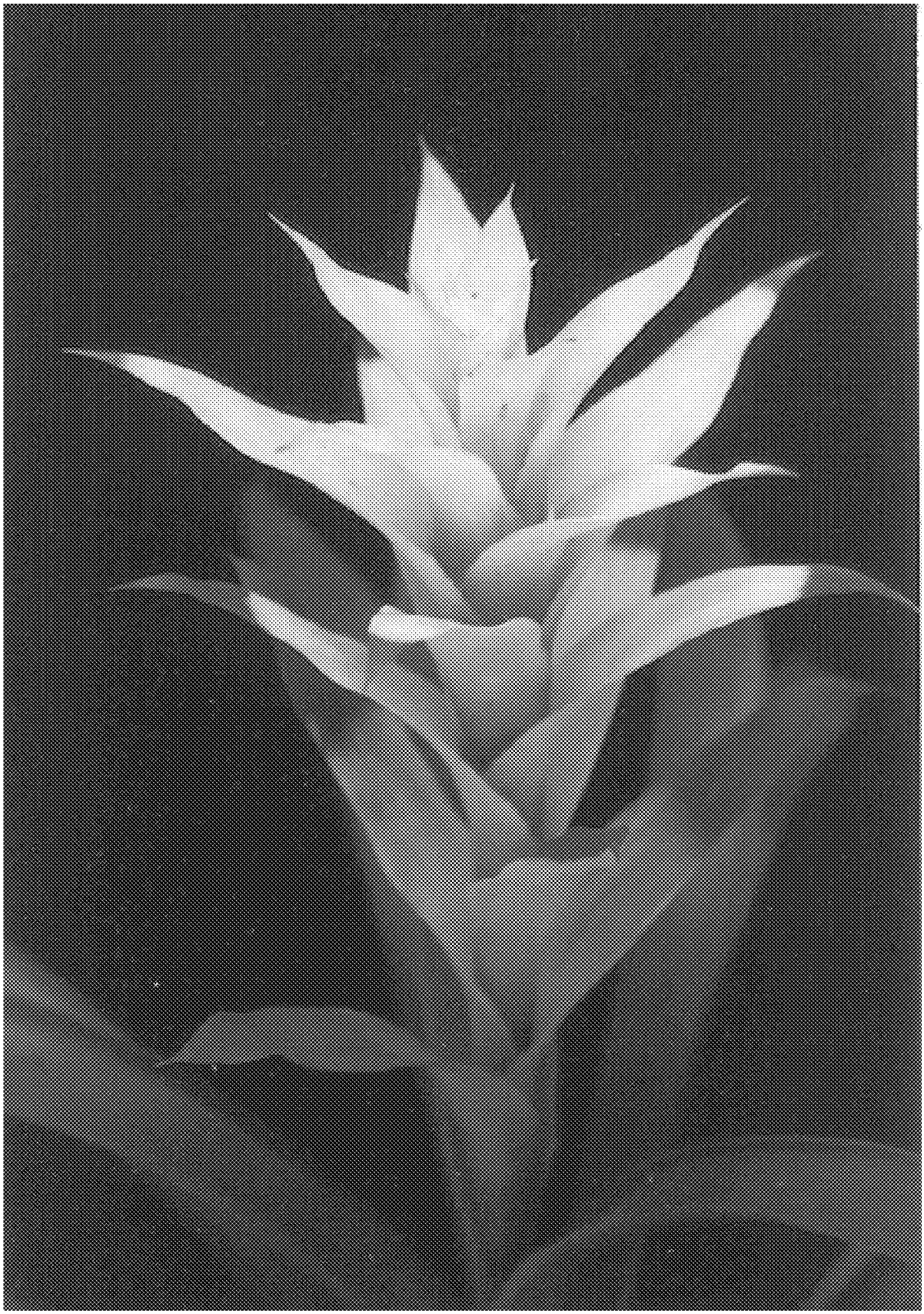

* * * * *